(12) United States Patent
Leitner et al.

(10) Patent No.: US 6,500,131 B2
(45) Date of Patent: Dec. 31, 2002

(54) CONTOUR MAPPING SYSTEM APPLICABLE AS A SPINE ANALYZER, AND PROBE USEFUL THEREIN

(75) Inventors: Josef Leitner, Tel Mond (IL); Florin Coter, Haifa (IL); Gideon E. Sturlesi, Bikat Beit Hakerem (IL); Adi Schechtman, Nofit (IL)

(73) Assignee: Orthoscan Technologies, Inc., Sherborn, MA (US)

(*) Notice: Subject to any disclaimer, the term of this patent is extended or adjusted under 35 U.S.C. 154(b) by 52 days.

(21) Appl. No.: 09/810,538

(22) Filed: Mar. 19, 2001

(65) Prior Publication Data

US 2002/0133097 A1 Sep. 19, 2002

(51) Int. Cl.$^7$ .............................................. A61B 5/103
(52) U.S. Cl. .................... 600/594; 600/409; 600/587
(58) Field of Search ................... 600/409, 587, 600/594

(56) References Cited

U.S. PATENT DOCUMENTS

| | | |
|---|---|---|
| 2,324,672 A | 7/1943 | Bierman et al. |
| 4,036,213 A | 7/1977 | Gregory |
| 4,521,685 A | 6/1985 | Rebman |
| 4,600,012 A | 7/1986 | Kohayakawa et al. |
| 4,664,130 A | 5/1987 | Gracovetsky |
| 4,730,625 A | 3/1988 | Fraser et al. |
| 4,760,851 A | 8/1988 | Fraser et al. |
| 5,042,505 A * | 8/1991 | Mayer et al. ............... 600/594 |
| 5,101,835 A | 4/1992 | DelRe |
| 5,181,525 A * | 1/1993 | Bunnell ...................... 600/594 |
| 5,251,127 A | 10/1993 | Raab |
| 5,303,480 A * | 4/1994 | Chek .......................... 600/587 |
| 5,471,995 A | 12/1995 | Halliday |
| 5,772,610 A | 6/1998 | McGorry et al. |
| 5,823,958 A | 10/1998 | Truppe |
| 5,989,201 A | 11/1999 | Brunner |
| 6,312,392 B1 * | 11/2001 | Herzon ....................... 600/587 |

FOREIGN PATENT DOCUMENTS

| | | | |
|---|---|---|---|
| DE | 4216458 A1 * | 12/1993 | ............ G01B/7/34 |
| DE | 4402562 A1 * | 8/1995 | ........... A61B/5/103 |
| EP | 305 780 | 3/1989 | |

* cited by examiner

Primary Examiner—Robin O. Evans
(74) Attorney, Agent, or Firm—G.E. Ehrlich Ltd.

(57) ABSTRACT

A contour mapping system useful as a spine analyzer includes a probe for application to a user's hand with the outer tip of at least one finger of the hand movable along the outer surface of the object (e.g., a person's spine) whose contour is to be mapped. A position sensor is carried by the probe and is movable therewith, and with the user's hand, as the user's finger moves along the outer surface of the object. The system further includes a position tracking system for tracking the movement of the position sensor as the probe is moved with the user's hand along the outer surface of the object.

37 Claims, 6 Drawing Sheets

CONTOUR MAPPING SYSTEM APPLICABLE AS A SPINE ANALYZER, AND PROBE USEFUL THEREIN

FIELD AND BACKGROUND OF THE INVENTION

The present invention relates to contour mapping systems for mapping the contour of an object. The invention is useful for mapping the curvature of the spine of a human being, for diagnosing spine deformities, such as scoliosis, and is therefore described below with respect to this application but could be used in many other applications. The invention also relates to a probe particularly useful in such a contour mapping system.

Scoliosis refers to a lateral spinal curve of a certain degree that affects an estimated 500,000 adults in the USA. The most common form of scoliosis, called idiopathic (i.e., of unknown origin) does not seem to have a real cause. There is a higher tendency to run in families with many more affected girls than boys; thus adolescent girls over the age of nine are five times more likely to be diagnosed with scoliosis than boys of the same age.

Early detection of the scoliosis can lead to effective treatment. Currently, scoliosis is treated by special braces, surgery, or by a combination of these techniques.

Screening for scoliosis detection has been adopted in most of the U.S. schools and in most of the Western World countries. Between 10 to 30% of the children that pass a simple examination at school are advised to visit a pediatrician/orthopedist for a more thorough investigation and eventually for a treatment recommendation. Approximately 30% of the latter are found to require long term treatment.

The basic tool for detecting scoliosis, and for quantifying the severity of the scoliosis, is the spinal roentgenogram (full length radiographs of the spine, one frontal and another sidewise). This is also the tool used by the physician during the long period of treatment and follow up.

Thus, a treated child will be exposed to a significant number of X-ray procedures, two to three double sessions per year. As a result, there is a concern about the late effects of this high dose radiation. Recent publications reveal a three to four times higher risk to develop breast cancer and a number of thyroid cancers in women undergoing repetitive X-ray exposures as part of their scoliosis treatment. In spite of efforts to reduce the radiation dose, there is still a higher lifetime risk of cancer from spinal radiographs among people with adolescent idiopathic scoliosis.

Therefore there is real need for an alternative device and system that will serve the same diagnostic purpose as the X-ray today but will eliminate the radiation exposure hazard especially for the young people. Multiple exposures during the long period of treatment are definitely a major factor that increases the risk of cancer.

A number of alternative systems have been developed, and are described in the literature, for measuring spine curvature in order to avoid the health hazard of radiation; see for example U.S. Pat. Nos. 2,324,672; 4,036,213; 4,600,012; 4,664,130; 4,760,851; 5,251,127; and 5,471,995. However, efforts are continually being made to develop systems and devices for measuring the spinal curve in a manner which enables more precision, and which can be performed more conveniently, than the existing systems.

OBJECTS AND BRIEF SUMMARY OF THE INVENTION

An object of the present invention is to provide a novel contour mapping system for mapping the contour of an object in a convenient and simple manner. Another object of the invention is to provide a contour mapping system which is useful for measuring the curvature of the spine of human beings in order to detect and/or treat for spine deformities, such as scoliosis.

According to one aspect of the present invention, there is provided a contour mapping system for mapping the contour of an object, comprising: a probe constructed for application to a user's hand with the outer tip of at least one finger of the hand movable along the outer surface of the object whose contour is to be mapped; a position sensor carried by the probe and movable therewith, and with the user's hand, as the at least one finger of the hand is moved along the outer surface of the object; and a position tracking system for tracking the movement of the position sensor as the probe is moved with the user's hand along the outer surface of the object.

One preferred embodiment of the invention is described below wherein the probe is constructed for grasping by the user's hand with the tip of at least one finger in a fixed position with respect to the position sensor carried by the probe. The described probe includes a handle graspable by the user's hand, and a finger supporting member fixed at one end of the handle for supporting the user's index finger at the fixed position with respect to the position sensor carried by the probe. The position sensor is within the finger supporting member which member is fixed substantially perpendicularly to the handle at one end thereof for supporting the user's finger with the tip of the finger exposed for direct contact with the outer surface of the object whose contour is to be mapped.

A second embodiment is described below wherein the probe is constructed for mounting on at least one finger of the user's hand, with the position sensor at a fixed position with respect to the finger tip. In that described embodiment, the probe is constructed for mounting on two adjacent fingers of the user's hand with the finger tips exposed for direct contact with the object whose contour is to be mapped.

In both embodiments described below, the object whose contour is to be mapped is the spine or the spinous processes of a person, and the system includes a data processor programmed to display data regarding the person's spine as mapped by the probe. The data processor may also be programmed to compute and to display the distance between adjacent vertebras in the mapped spinal column, and/or the Cobb angle between adjacent vertebras in the mapped spinal column.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
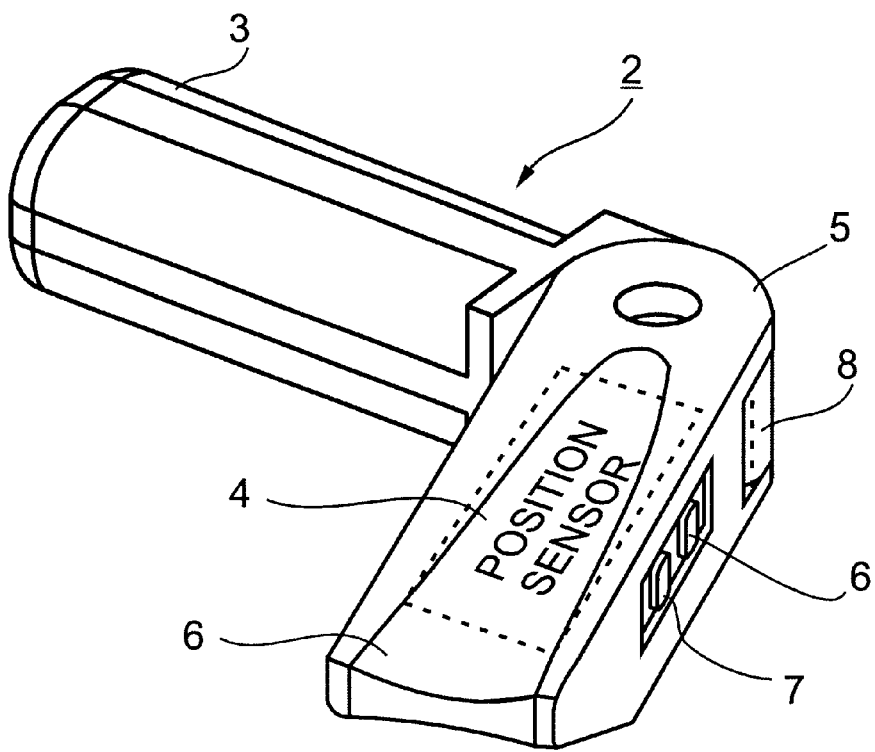
FIG. 1 is a three-dimensional view illustrating one form of probe constructed in accordance with the present invention.
Figure 2:
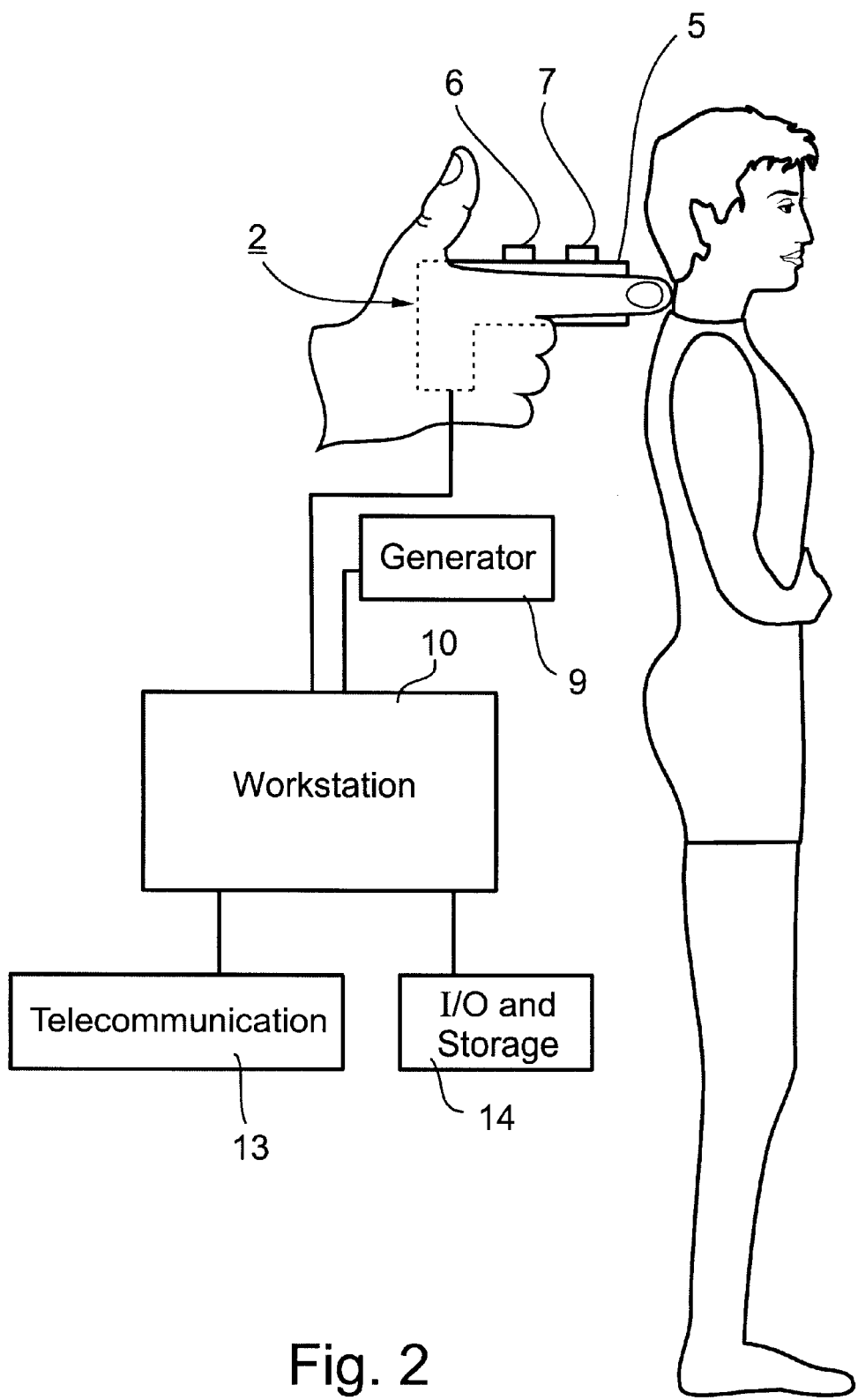
FIG. 2 illustrates the use of the probe of FIG. 1 in a computerized spine analyzer system for measuring the curvature or other characteristics of the spine of a person.

FIG. 1 illustrates one form of probe, therein generally designated 2, to be used in the manner shown in FIG. 2 for mapping the curvature of a person's spine, e.g., in order to detect the presence, and the degree if present, of a deformation in the spine, such as scoliosis. As will be described more particularly below, and as shown in FIG. 2, the probe 2 is constructed such that when it is grasped by a user's hand, the outer tip of the index finger of the user's hand is fixed with respect to a position sensor carried by the probe and is movable along the outer surface of the subject's spine. Tracking the movements of the index finger thereby provides a measurement of the curvature of the spine along which it is moved.

Probe 2 illustrated in FIG. 1 includes a handle 3 graspable by the hand of the user, and a position sensor 4 for use in tracking the movements of the probe. Position sensor 4 is carried by a finger-supporting member 5 extending substantially perpendicularly from one end of the handle 3 and formed with a groove 6 for receiving the index finger of the user's hand grasping the handle 3. The finger-supporting member 5 is of a length less than the length of the user's index finger, so that the outer tip of the user's index finger is exposed for contact with the outer surface of the spine whose curvature is to be mapped, as shown in FIG. 2.

Probe 2 further includes a depressible button 6 depressible by the thumb of the user's hand to enter into the position tracking system the location of the position sensor 4 at the instant the button is depressed.

FIG. 1 illustrates the probe 2 as having a second button 7, next to button 6, and also depressible by the thumb of the user. Button 7 may be used for canceling a previous entry, or for canceling all the previous entries. For example, the tracking system can be programmed such that a short depression of button 7 cancels the previous entry, whereas a long depression of the button clears the system of all the previous entries for the respective operation.

Probe 2 may also include an audible or visual signaling device 8 for providing an appropriate signal when a reading has been properly entered.

When probe 2 is used, as shown in FIG. 2, for mapping the curvature of a person's spine, the movements of the position sensor 4, which correspond to the curvature of the person's spine, are tracked by a position tracking system included within a data processor in a workstation described below with respect to FIG. 2. Many position tracking systems are known in the prior art for the determination of the position of an object in a three-dimensional space. Such systems, once calibrated and normalized, track the movements of the object to thereby determine its actual position at all times. The known position tracking systems include mechanical, acoustical, radio-frequency, magnetic, electromagnetic and optical systems for tracking the movements of the object. Examples of such position tracking systems based on acoustical or electromagnetic fields are disclosed in, for example, U.S. Pat. Nos. 5,412,619; 6,083,170; 6,063,022; 5,954,665; 5,840,025; 5,718,241; 5,713,946; 5,694,945; 5,568,809; 5,546,951; 5,480,422 and 5,391,199, which patents are incorporated herein by reference.

In the preferred embodiment of the invention illustrated in FIG. 2, the position tracking system is of the electromagnetic field type. It includes a transmitter 9 for generating a magnetic field in the space occupied by the person's spine to be mapped. The position sensor 4 within the probe 2 is a tri-axial magnetic sensor for sensing the instantaneous position of the probe within the generated magnetic field. Both the transmitter 9 and the position sensor 4 produce signals which are applied to the workstation, generally designated 10, which tracks the movement of the position sensor 4, and thereby of the probe 2, as the probe is moved with the user's hand along the outer surface of the subject's spine.

Figure 3:
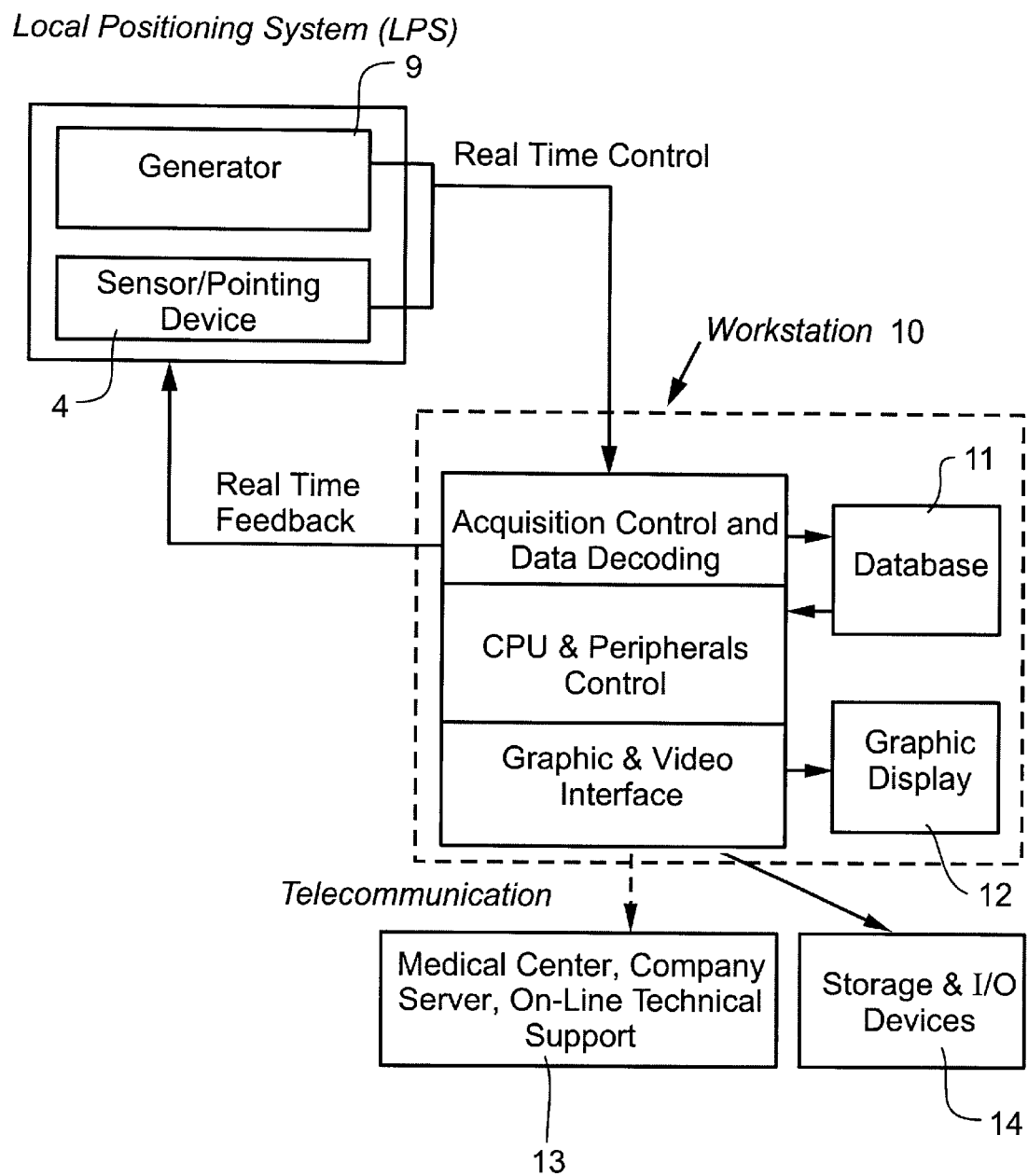
FIG. 3 is a block diagram illustrating the electrical circuit in the system of FIG. 2.

The overall electrical system is illustrated in the block diagram of FIG. 3. As shown in FIG. 3, the workstation 10 receives real-time control inputs from both the position sensor 4 and the transmitter 9, and produces real-time feedback to the position sensor in order to track the movements of the position sensor, and thereby of the probe. The workstation 10 includes a database 11 for storing data during the processing thereof, and a graphic display 12 for displaying the processed data. Communication with the database 11 is via a CPU and peripheral controls within the workstation 10, as well as acquisition control and data decoding circuitry. Communication with the graphic display 12 is via graphic and video interface circuitry within the workstation 10.

The workstation 10 may process the inputted information according to the following algorithm:

(1) Read n points (n=10 ... 18), with each reading being taken by feeling the spinous process using the scanner and getting the point's coordinates and convert the points into a curve using a mathematical curve fitting function;

(2) Fit a built-in Spine module with fixed vertabreas to the curve;

(3) Determine the position of each vertebra (XYZ axes and angles);

(4) Run a correction function (based on wide statistics researches) to convert the spinous process curve to the curve which passes through the middle of the vertebras;

(5) Calculates the Cobb angle and determine the vertebras that define it.

The workstation 10 is also provided with a telecommunication channel for communicating with remotely-located medical centers, company servers, on-line technical support, and the like, as indicated by block 13 in FIG. 3. The workstation 10 further communicates with a storage device, and with input-output (I-O) devices, as indicated by block 14 in FIG. 3.

It will thus be seen that the described system enables data representing or relating to the spine curvature to be obtained in a manner which is free of the health hazards characteristic of the presently-used X-ray equipment. The novel system allows frequent monitoring of the spinal curvature so as to permit a progressive analysis of the development of scoliosis based on consecutive scanning. If X-ray pictures have already been taken of the particular subject, the described system allows an augmented presentation of such X-ray pictures with the graphical presentation of the data acquired by the use of the equipment. The system also allows analysis of any requested parameters, such as determination and display of the distance between vertebras and the spine deformity angle or the Cobb angle. It can also provide data about rotation, chest rib deformity (not normally provided by X-rays), leg height discrepancies, etc. The described system also enables dynamic spine analysis (during bending), and limited space motion analysis (during movements).

For example the data processor may be programmed to display the dynamic movement of the spine while a point on the spine is contacted by the probe. Thus, the physician can touch a point on the spine, and while the patient is bending forwardly or sidewardly, e.g., at 90 degrees (Adams test), at 45 degrees, etc., data can be accumulated which can be integrated to simulate dynamical movement of the spine and indicate the degree of chest deformity and rotation.

Figure 4:
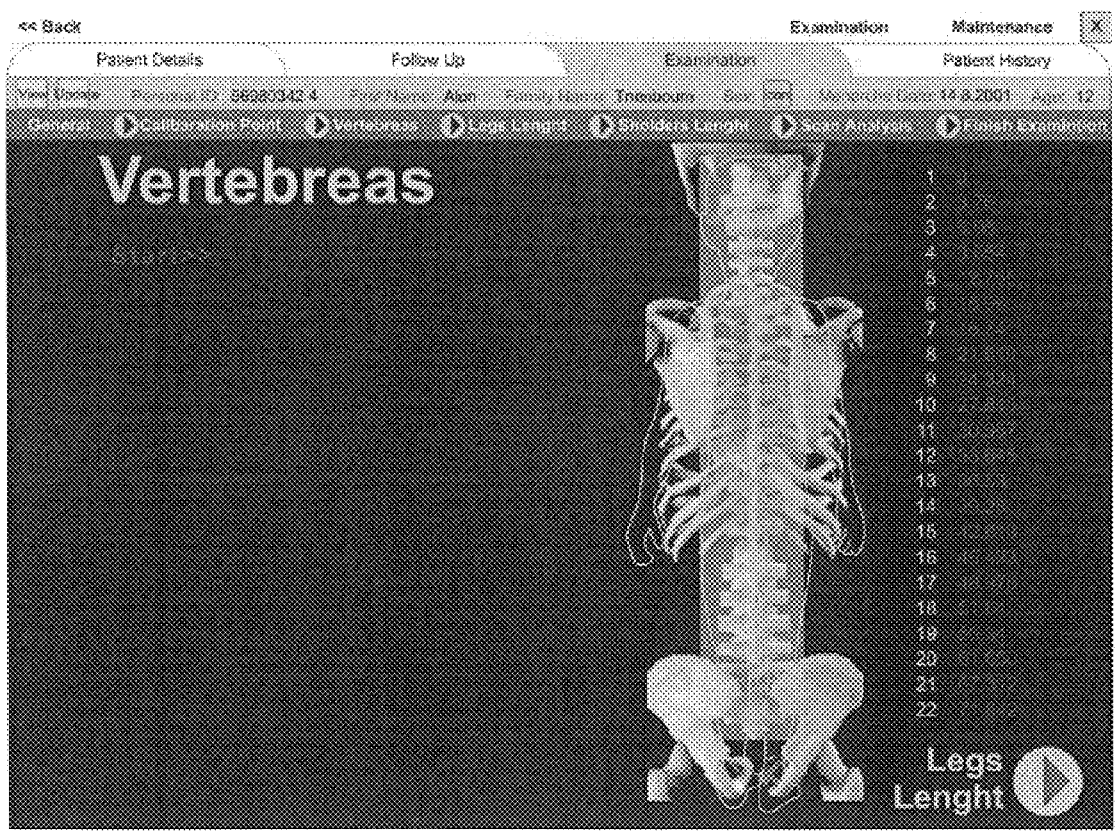
FIG. 4 illustrates an example of a display produced by the use of the computerized spine analyzer system of FIGS. 2 and 3.

FIG. 4 illustrates an example of a graphical display that may be produced by the described system. Thus, the vertebras of the subject can be displayed, e.g., by previously taken X-rays of the respective subject; and the location of each vertebra in the spine can be indicated on the displayed spine. The distance of each vertebrae from the adjacent vertebrae can also be calculated and displayed. If the patient is suffering from scoliosis, the development of the scoliosis, as well as the effects of any remedial treatment, can be continuously monitored.

Figures 5A, 5B:
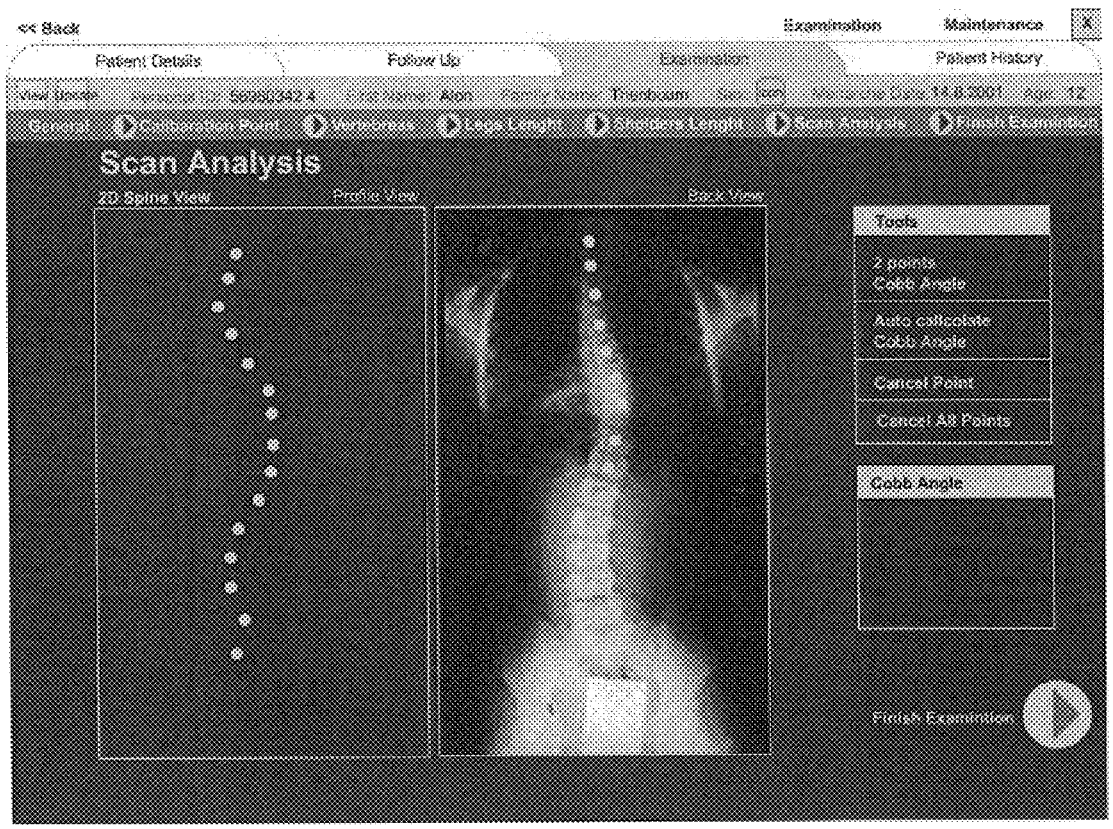
FIG. 5a illustrates a 2-D profile view of the spine.
FIG. 5b illustrates a 2-D back AP or CORONAL view of the spine, produced by the computerized spine analyzer system of FIGS. 2 and 3.

FIG. 5a illustrates a graphical display of a profile view, and FIG. 5b illustrates a graphical display of a back view that may be produced by the described system. Such views can be used for determining and displaying the Cobb angle between two vertebras.

It will thus be seen that the present invention utilizes the user's finger as the "feeling part" of the probe. This not only simplifies the construction of the probe, but also exploits the sense of touch for following the curvature to be mapped. Such a system is therefore particularly useful for mapping the curvature of a person's spine, but it will be appreciated that it could be used in other applications involving the mapping of the contour of an object.

Figure 6:
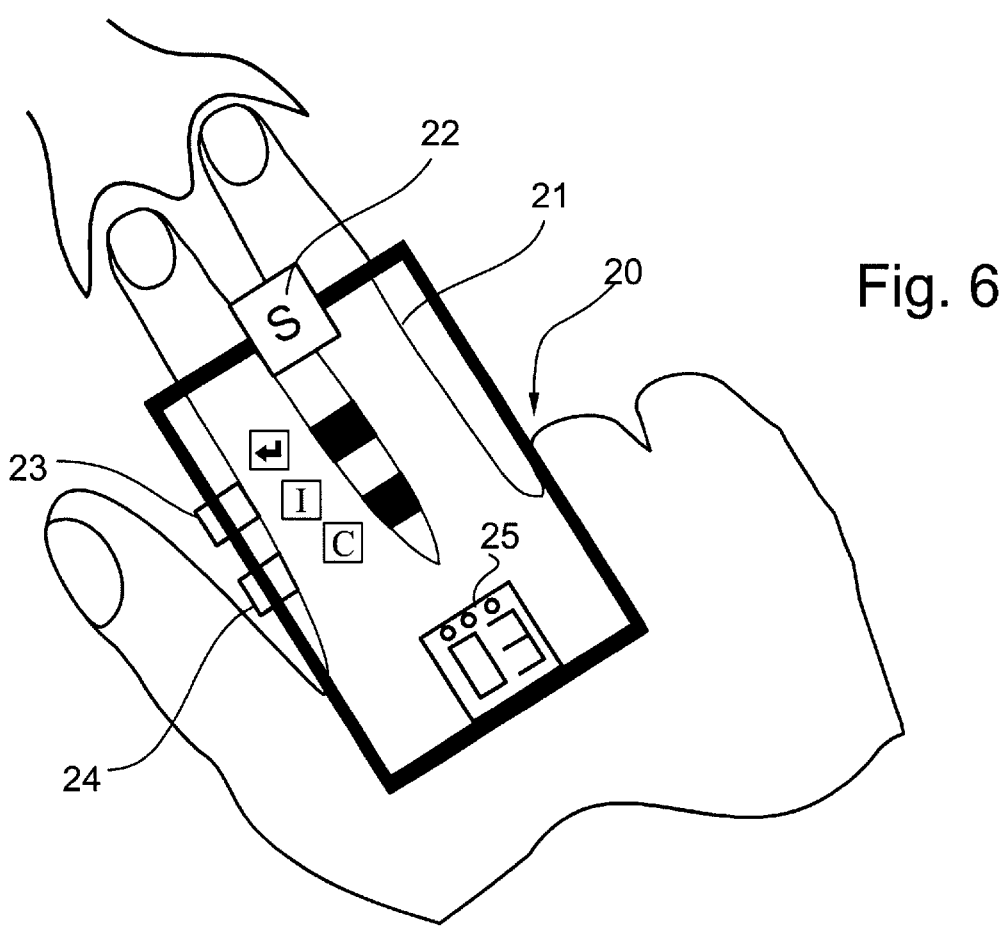
FIG. 6 illustrates a second form of probe constructed in accordance with the present invention.

FIG. 6 illustrates another construction of probe, therein generally designated 20, which may also be used for this purpose. The probe 20 illustrated in FIG. 7 is mounted on at least one finger, and preferably on two fingers, of the user.

Thus, probe 20 illustrated in FIG. 6 includes a housing 21 mountable on two fingers such as to expose the outer tips of the two fingers for direct contact with the spine (or other object whose contour is to be monitored). Housing 21 includes a position sensor 22 for sensing the instantaneous position of the probe in space, e.g., in the same manner as described above with respect to FIGS. 1–3. Probe 20 further includes a depressible button 23 for entering the instantaneous location of the position sensor, and a second depressible button 24 for clearing previous entries, in the same manner as described above with respect to probe 2 illustrated in FIG. 1. Probe 20 in FIG. 6 may also include a display 25, which may be used for displaying each entry, or for displaying any of the calculations produced by the workstation, (e.g., the Cobb angle, the distance between it and the adjacent vertebrae, etc.) produced by the workstation 10 during an examination procedure. Such a display may also be included in probe 2 illustrated in FIG. 1; and similarly, probe 20 illustrated in FIG. 6 could also include an audible signal to indicate that an entry has been made, as in probe 2 illustrated in FIG. 1.

Probe 20 illustrated in FIG. 6, would otherwise be constructed and used in the same manner as probe 2 as described above.

Figure 7:
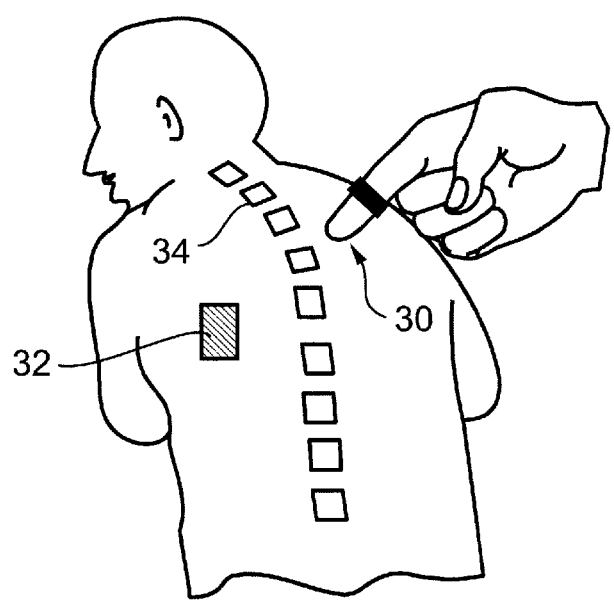
FIG. 7 illustrates a further embodiment of the invention wherein the system includes a reference position sensor, or a magnetic field generator, fixed to the object (e.g., the back of the person whose spine is to be mapped), whereby the position tracking system tracks the movement of the position sensor with respect to that reference.

FIG. 7 illustrates the probe, therein generally designated 30, used with a reference sensor, generally designated 32, attached to the person's body at a fixed and known location with respect to the spine 34. Thus, the position tracking system will track the movements of the probe 30 with respect to the reference 32; and since the position of the reference 32 is known with respect to the spine 34, the system will be able to track the movement of the probe also with respect to the spine. Such an arrangement makes the system sensitive only to the changes in position of the probe 30 with respect to the reference 32, and enables the system to ignore the change in position of the body generally in space. The system illustrated in FIG. 7, therefore, is particularly useful for displaying the dynamic movements of the spine during forward and sideward bending movements.

Reference sensor 32 may be another position sensor which serves as a reference with respect to probe 30, or may be the magnetic field generator itself which also thereby serves as a reference with respect to probe 30.

It will thus be seen that the illustrated probes utilize the tactile sense of the user to indicate to the user whether a position sensed by the probe should be entered into the position tracking system. In the probes of FIGS. 1, 6 and 7, the entry command is effected by depressing a push button, but other arrangements could be used. For example, the entry command could be effected by an electrical switch which is actuated by contact of the probe or the user's finger with the object, (e.g., the person's spine) to be mapped, or which is actuated by a proximity detector when at predetermined proximity from the object. The entry command could also be effected by a foot pedal, or by a voice-responsive device.

In addition, the data may be entered continuously to map the spinal column or other object. Alternatively, the data may be entered in the form of selected samples, which samples could be used, by either interpolation or extrapolation, for deriving any desired information regarding the spinal column or other object being mapped.

Further, while the preferred embodiments described above utilize an electromagnetic-field position tracking system for tracking the movements of the probe, it will be appreciated that other forms of position tracking systems could be used, such as optical systems, sonic systems, articulated arm systems, and other such systems well known in the art.

Therefore, while the invention has been described with respect to preferred embodiments, it will be appreciated that these are set forth merely for purposes of example, and that many other variations, modifications and applications of the invention may be made.

What is claimed is:

1. A contour mapping system for mapping the contour of an object, comprising:

a probe constructed for application to a user's hand with the outer tip of at least one finger of the hand movable along the outer surface of the object whose contour is to be mapped;

a position sensor carried by said probe and movable therewith, and with the user's hand, as said at least one finger of the hand is moved along the outer surface of said object;

and a position tracking system for tracking the movement of said position sensor as the probe is moved with the user's hand along the outer surface of said object.

2. The system according to claim 1, wherein said probe is constructed for grasping by the user's hand with the tip of said at least one finger in a fixed position with respect to said position sensor carried by the probe.

3. The system according to claim 2, wherein said probe includes a handle graspable by the user's hand, and a finger supporting member fixed at one end of said handle for supporting the user's index finger at said fixed position with respect to the position sensor carried by the probe.

4. The system according to claim 3, wherein said finger supporting member is fixed to said handle at one end thereof for supporting the user's index finger with the tip of the finger exposed for direct contact with the outer surface of the object whose contour is to be mapped.

5. The system according to claim 4, wherein said finger supporting member is formed with a groove for receiving said index finger of the user's hand.

6. The system according to claim 1, wherein said probe is constructed for mounting on said at least one finger of the user's hand, with said position sensor at a fixed position with respect to the finger tip.

7. The system according to claim 6, wherein said probe is constructed so as to expose said finger tip for direct contact with the outer surface of the object whose contour is to be mapped.

8. The system according to claim 7, wherein said probe is constructed for mounting on two adjacent fingers of the user's hand with the finger tips exposed for direct contact with the object whose contour is to be mapped.

9. The system according to claim 1, wherein said position tracking system includes a magnetic field generator for generating a magnetic field in the space occupied by said object, and said position sensor of the probe is a magnetic sensor for sensing the instantaneous position of the probe within said magnetic field.

10. The system according to claim 1, wherein said position tracking system is included in a workstation which further includes a data processor and a display for displaying data corresponding to the instantaneous positions of the probe as it is moved along the outer surface of said object.

11. The system according to claim 10, wherein said data processor further includes a storage device for storing said displayed data in a manner enabling it to be retrieved for comparison with corresponding data obtained by subsequently mapping said object.

12. The system according to claim 10, wherein the object whose contour is to be mapped is the spine of a person, and said data processor is programmed to display data regarding the person's spine as mapped by said probe.

13. The system according to claim 12, wherein said data processor is also programmed to compute and display the distance between adjacent vertebras in the mapped spine.

14. The system according to claim 12, wherein said data processor is also programmed to compute and display the Cobb angle between adjacent vertebras in the mapped spine.

15. The system according to claim 12, wherein said data processor is also programmed to store the data produced during one spine mapping operation, and to compare said data with the data produced during a subsequent spine mapping operation of the same person.

16. The system according to claim 12, wherein said data processor is also programmed to display the dynamic movements of the spine while a point on the spine is contacted by the probe.

17. The system according to claim 1, wherein said system further comprises a reference fixed to said object, and said position tracking system tracks the movement of said position sensor with respect to said reference.

18. The system according to claim 17, wherein said position sensor is a magnetic sensor, and said reference fixed to said object is a magnetic field generator which serves as a reference with respect to said magnetic sensor.

19. The system according to claim 1, wherein said probe includes an electrical switch which is manually actuated to enter the respective position of the probe into said position tracking system.

20. The method according to claim 1, wherein said probe includes an electrical switch which is actuated by contact with the object to enter the respective position of the probe into said position tracking system.

21. The method according to claim 1, wherein said probe includes an electrical switch which is actuated by proximity with the object to enter the respective position of the probe into said position tracking system.

22. The method according to claim 1, wherein said position tracking system is an electromagnetic system.

23. The method according to claim 1, wherein said position tracking system is an optical system.

24. The method according to claim 1, wherein said position tracking system is a sonic system.

25. The method according to claim 1, wherein said position tracking system is an articulated-arm system.

26. A probe for use in a contour mapping system, said probe being constructed for application to a user's hand with the outer tip of at least one finger of the user's hand movable along the outer surface of the object whose contour is to be mapped; said probe further including a position sensor sensing the position of the probe as it is moved by the user's hand along the outer surface of the object whose contour is to be mapped.

27. The probe according to claim 26, wherein said probe further comprises a depressible button depressible by the thumb of the user's hand to enter into said position tracking system the location of said position sensor at the instant the button is depressed.

28. The probe according to claim 26, wherein said probe is constructed for grasping by the user's hand with the tip of at least one finger in a fixed position with respect to said position sensor carried by the probe.

29. The probe according to claim 26, wherein said probe includes a handle graspable by the user's hand, and a finger supporting member fixed at one end of said handle for supporting the user's index finger at said fixed position with respect to the position sensor carried by the probe.

30. The probe according to claim 26, wherein said position sensor is fixed within said finger supporting member which member is fixed at one end thereof for supporting the user's finger with the tip of the finger exposed for direct contact with the outer surface of the object whose contour is to be mapped.

31. The probe according to claim 25, wherein said probe is constructed for mounting on said at least one finger of the user's hand, with said position sensor at a fixed position with respect to the finger tip.

32. The probe according to claim 31, wherein said probe is constructed so as to expose said finger tip for direct contact with the outer surface of the object whose contour is to be mapped.

33. The probe according to claim 32, wherein said probe is constructed for mounting on two adjacent fingers of the user's hand with the finger tips exposed for direct contact with the object whose contour is to be mapped.

34. The probe according to claim 26, wherein said position sensor is a magnetic sensor for sensing the instantaneous position of the probe within a magnetic field.

35. The probe according to claim 26, wherein said position sensor is an optical sensor.

36. The probe according to claim 26, wherein said position sensor is a sonic sensor.

37. The probe according to claim 26, wherein said position sensor is an articulated-arm sensor.

* * * * *